United States Patent
Robins

(10) Patent No.: US 6,642,211 B2
(45) Date of Patent: Nov. 4, 2003

(54) TREATMENT OF CANCER WITH THYMIDINE IN COMBINATION WITH TEMOZOLAMIDE

(75) Inventor: H. Ian Robins, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 10/114,291

(22) Filed: Apr. 1, 2002

(65) Prior Publication Data

US 2002/0198183 A1 Dec. 26, 2002

Related U.S. Application Data

(60) Provisional application No. 60/282,025, filed on Apr. 6, 2001.

(51) Int. Cl.[7] .......................... A61K 31/70; A61K 31/33
(52) U.S. Cl. ........................................... 514/50; 514/183
(58) Field of Search ..................................... 514/183, 50

(56) References Cited

U.S. PATENT DOCUMENTS

2002/0009428 A1 * 1/2002 Zaknoen ..................... 514/183

OTHER PUBLICATIONS

Robins et al., Proc. Am. Soc. Clin. Oncol. (19, 36 Meet., 166a, 2000) Abstract Only.*
Brock et al., Cancer Research (Oct. 1, 1998), vol. 58, pp 4363–4367 Abstract Only.*

* cited by examiner

Primary Examiner—Jerome D Goldberg
(74) Attorney, Agent, or Firm—Licata & Tyrrell P.C.

(57) ABSTRACT

Methods for treating cancer are provided that involve administration of a combination of the chemotherapeutic drug, temozolamide, and thymidine.

4 Claims, No Drawings

TREATMENT OF CANCER WITH THYMIDINE IN COMBINATION WITH TEMOZOLAMIDE

This application claims the benefit of priority from U.S. provisional application Serial No. 60/282,025, filed Apr. 6, 2001.

This application claims the benefit of priority from U.S. provisional application Serial No. 60/282,025, filed Apr. 6, 2001. This invention was-supported in part by funds from the U.S. government (NIH Grant No. CA62421) and the U.S. government may therefore have certain rights in the invention.

BACKGROUND OF THE INVENTION

Temozolamide is the first drug approved by the United States Food and Drug Administration in over 50 years for the treatment of brain tumors. It is an imidazole tetrazinone compound and has demonstrated clinical efficacy in the treatment of high grade gliomas and malignant melanoma. Resistance to temozolamide therapy has been reported to develop due to the activity of poly (ADP-ribose) polymerase (Tentori et al. 1997. *Mol. Pharmacol.* 52:249–258; Wedge et al. 1996. *Br. J. Cancer* 74:1030–1036). Like most chemotherapeutic agents, the dose-limiting toxicity of the drug is related to myelosuppression.

Thymidine is a naturally occurring nucleoside metabolite which preferentially kills neoplastic cells in vitro and induces partial regression of a wide variety of human tumor xenografts, including malignant glioma (O'Dwyer, P. J. et al. 1987. *Cancer Res.* 47:3911–3919; Cohen, J. D. et al. 1989. *Cancer Res.* 49:5805–5809; Cohen, J. D. et al. 1990. *J. Neurooncol.* 9:1–8). The mechanism of action of this nucleotide is related to the intracellular triphosphorylation that occurs which leads to triphosphate modulation of ribonucleotide reductase, resulting in deoxycytidine starvation, an increase in deoxyguanosine triphosphate, and an inhibition of poly (ADP-ribose) polymerase. Inhibition of this key DNA repair enzyme results in cessation of DNA synthesis, inhibition of DNA repair, and cell death (O'Dwyer, P. J. et al. 1987. *Cancer Res.* 47:3911–3919).

Prolonged infusions with thymidine of up to 30 days in patients with leukemia have resulted in anti-cancer activity but also significant myelotoxicity (Kufe, D. W. et al. 1980. *Blood* 55:580–589). Shorter infusions of high dose thymidine, however, have been shown to be effective and free of the myelosuppressive activity that is usually dose-limiting (Cohen, J. D. et al. 1990. *J. Neurooncol.* 9:1–8).

Recent studies have examined the combined treatment with a known chemotherapeutic agent, carboplatin, and thymidine. The combination therapy was initiated based on studies in cells that showed that inhibition of poly (ADP-ribose) polymerase activity results in enhancement of the anti-neoplastic activity of carboplatin (Cohen, J. D. et al. 1989. *Cancer Res.* 49:5805–5809; Cohen, J. D. et al. 1990. *J. Neurooncol.* 9:1–8). The sensitization of cells to the effects of carboplatin increased as thymidine exposure increased, up to 16 hours, until the effect reached a plateau. In initial clinical studies, the pharmacokinetics of the thymidine-carboplatin interaction were studied. Thymidine was shown not to affect the pharmacokinetics or protein binding of carboplatin (Robins, H. I. et al. 1999. *J. Clin. Oncol.* 17:2922–2931). Three of the six patients in the study, being treated for recurrent malignant glioma, showed at least partial disease remission. In addition, thymidine was shown to protect against dose-limiting carboplatin myelotoxicity.

Following completion of the Phase I study with thymidine and carboplatin in combination therapy, a Phase II recurrent high-grade glioma study was initiated (Robins, H. I. et al. 2000. *Proceedings of the American Society for Clinical Oncology* 19:166a). initiated (Robins, H. I. et al. 2000. *Proceedings of the American Society for Clinical Oncology* 19:166a). Consistent with the results of the Phase I study, thymidine was myeloprotective, resulting in a minimal need for dose reduction due to myelotoxicity.

There continues to be a need for effective treatment regimens in a variety of cancers, including recurrent brain cancer, where the combination of therapeutics results in either an enhanced clinical efficacy and/or a reduced occurrence of adverse side effects which would allow for administration of higher doses of effective chemotherapeutics.

SUMMARY OF THE INVENTION

An object of the present invention is a method for treating cancer which comprises administration of a combination of thymidine and temozolamide.

Another object of the present invention is a method for reducing dose-limiting toxicity of a chemotherapeutic drug which comprises administration of thymidine in combination with the chemotherapeutic, temozolamide.

Yet another object of the present invention is a method for increasing the efficacy of a chemotherapeutic drug in the treatment of cancer which comprises administration of thymidine in combination with the chemotherapeutic, temozolamide.

DETAILED DESCRIPTION OF THE INVENTION

It has now been found that combining thymidine with a chemotherapeutic drug in the treatment of cancer results in protection against the dose-limiting toxicity often associated with cancer treatment, myelosuppression. Temozolamide is an approved chemotherapeutic drug for treatment of glioma in humans. However, like many anti-cancer agents, the dose administered is limited by the myelosuppression that results in patients undergoing cancer treatment. Combination of thymidine with temozolamide will result in a reduction in dose-limiting toxicity, which will allow for administration of higher doses to patients for treatment of cancer. In addition, based on the fact that temozolamide resistance is due to activity of poly (ADP-ribose) polymerase, the inhibition of this enzyme by thymidine will result in a synergistic cytotoxic interaction between temozolamide and thymidine, which will produce an increased efficacy of the combination therapy in the treatment of cancer over administration of temozolamide alone.

Patients will be recruited for a Phase I/II study of the clinical efficacy and toxicity of combination therapy with thymidine (24 hour infusion at a dose of 75 g/m$^2$) and temozolamide (oral dosing at hour 20 of the infusion, doses of 750 mg/m$^2$ in previously treated patients and 1000 mg/m$^2$ in patients with no prior therapy). Temozolamide will be given with emetics. The temozolamide dose will be escalated or de-escalated depending on the level of toxicity reported, with dose changes of 150 mg/m$^2$ based on the previous cycle's level of myelosuppression. The patient population will be recurrent high grade glioma that has been histologically confirmed. All patients will be required to give written informed consent. Also required will be adequate bone marrow function (white blood cell count $\geq 3.4 \times 10^3$ per $\mu$l and platelet count $\geq 100 \times 10^3$ per $\mu$l), adequate hepatic function (total bilirubin level $\leq 1.5$ mg/100 ml) and adequate liver function test results (less than three times normal levels of alkaline phosphatase, lactate dehydrogenase, and serum glutamate transferase) as well as adequate renal function (creatinine level less than 1.5 mg/dL or creatinine clearance $\geq 60$ ml/min, blood urea nitrogen $\leq 30$ mg/dL), with calcium and electrolytes within normal limits.

Patients with certain types of clinical histories will also be screened out from the study such as a history of congestive heart failure, ongoing cardiac dysrhythmia, uncontrolled hypertension, or AIDS. Also excluded from the study will be patients with more than 25% of their marrow having been irradiated.

Patients on study will be monitored for the occurrence of dose-limiting toxicity such as thrombocytopenia and/or neutropenia. In addition, the following clinical endpoints will be monitored: survival, response rate, and time to treatment failure.

The present invention is therefore a method for treating cancer, including but not limited to glioma and malignant melanoma, ovarian cancer and breast cancer. The method of the present invention involves administration of the combination of thymidine with an effective dose of a chemotherapeutic drug, temozolamide. In the context of the present invention "an effective dose" is a dose of the chemotherapeutic drug known to have anti-cancer activity either in vitro in cells or in vivo in animals, including humans. One of skill would choose such an effective dose based on the results of clinical studies of the drug when administered alone or on data showing pharmacological activity in cells or animals, including humans. Also contemplated by the present invention are the combination of any other chemotherapeutic drug that produces dose-limiting myelosuppression and/or has resistance linked to the activity of poly (ADP-ribose) polymerase. The present invention is therefore also a method for reducing dose-limiting toxicity of a chemotherapeutic drug which comprises administration of thymidine in combination with the chemotherapeutic, temozolamide. Finally, the present invention is a method for increasing the efficacy of a chemotherapeutic drug in the treatment of cancer which comprises administration of thymidine in combination with the chemotherapeutic, temozolamide.

What is claimed is:

1. A method for reducing myelosuppression associated with temozolomide administration in a patient comprising administering to a patient an effective dose of temozolomide in combination with thymidine wherein said thymidine inhibits poly (ADP-ribose) polymerase activity producing a synergistic cytotoxic interaction between the thymidine and the temozolomide so that a greater than additive effect of temozolomide and thymidine is realized.

2. A method for reducing the dose-limiting toxicity of temozolomide comprising administering to a patient an effective amount of temozolomide in combination with thymidine wherein said thymidine inhibits poly (ADP-ribose) polymerase activity producing a synergistic cytotoxic interaction between the thymidine and the temozolomide so that a greater than additive effect of temozolomide and thymidine is realized.

3. A method for increasing the efficacy of temozolomide in the treatment of cancer comprising administering to a patient an effective amount of temozolomide in combination with thymidine wherein said thymidine inhibits poly (ADP-ribose) polymerase activity producing a synergistic cytotoxic interaction between the thymidine and the temozolomide so that a greater than additive effect of temozolomide and thymidine is realized and wherein the cancer is sensitive to the combination of thymidine and temozolomide.

4. The method of claim 1 wherein the cancer is glioma.

* * * * *